US008895767B2

(12) United States Patent
Araneda Herrera

(10) Patent No.: US 8,895,767 B2
(45) Date of Patent: Nov. 25, 2014

(54) OBTAINING FATTY ACIDS FROM INSECT LARVAE

(75) Inventor: Benjamin Patricio Araneda Herrera, Vina del Mar (CL)

(73) Assignee: Investigación y Comercialización Biotecnológica Omebit S.A, Santiago (CL)

( * ) Notice: Subject to any disclaimer, the term of this patent is extended or adjusted under 35 U.S.C. 154(b) by 349 days.

(21) Appl. No.: 13/384,324

(22) PCT Filed: Jun. 11, 2010

(86) PCT No.: PCT/CL2010/000022
§ 371 (c)(1),
(2), (4) Date: Jan. 16, 2012

(87) PCT Pub. No.: WO2011/006276
PCT Pub. Date: Jan. 20, 2011

(65) Prior Publication Data
US 2012/0123141 A1  May 17, 2012

(30) Foreign Application Priority Data

Jul. 14, 2009 (CL) .................................. 1586-2009

(51) Int. Cl.
| | |
|---|---|
| *A01H 5/00* | (2006.01) |
| *A23D 9/00* | (2006.01) |
| *C02F 1/00* | (2006.01) |
| *B01D 37/00* | (2006.01) |
| *A61K 35/64* | (2006.01) |
| *A23K 1/16* | (2006.01) |
| *A23K 1/18* | (2006.01) |
| *C11B 3/12* | (2006.01) |
| *C11B 1/10* | (2006.01) |
| *C11B 1/02* | (2006.01) |
| *C11B 5/00* | (2006.01) |
| *A01K 67/033* | (2006.01) |
| *A23L 1/30* | (2006.01) |

(52) U.S. Cl.
CPC ............... *A23D 9/00* (2013.01); *A61K 35/642* (2013.01); *A23K 1/164* (2013.01); *A23K 1/1873* (2013.01); *C11B 3/12* (2013.01); *C11B 1/10* (2013.01); *C11B 1/02* (2013.01); *C11B 5/00* (2013.01); *A01K 67/033* (2013.01); *A23L 1/3006* (2013.01)
USPC ........................... 554/223; 554/224; 210/770

(58) Field of Classification Search
USPC .................................. 554/223, 224; 210/770
See application file for complete search history.

(56) References Cited

U.S. PATENT DOCUMENTS

2002/0177219 A1   11/2002   Olivier
2003/0233982 A1   12/2003   Zhang

FOREIGN PATENT DOCUMENTS

| CN | 1869180 A | 11/2006 |
|---|---|---|
| CN | 101032525 A | 9/2007 |

OTHER PUBLICATIONS

Salazar-Govea Alma, Y et al. Extracccion supercrtica of acidos grasos of larva of mosca comun. Musca domestica. Memorias dthe XXII Congreso Nacional ofTermodinamica. 440-449. Toluca, Estado of Mex ico. Septcmber of 2007.*
American Heart Association; "Fish and Omega-3 Fatty Acids" 2007; online at http://heart.org/HEARTORG/GettingHealthy/.../Fish-and-Omega-3-Fatty-Acids_UCM_303248_Article.jsp; 1 page.
M. Bousquet, et al; "Beneficial effects of dietary omega-3 polyunsaturated fatty acid on toxin-induced neuronal degeneration in an animal model of Parkinson's disease", The FASEB Journal; Epub Nov. 21, 2007 vol. 22, Issue 4; pp. 1213-1225.
E A M De Deckere; "Possible beneficial effect of fish and fish n-3 polyunsaturated fatty acids in breast and colorectal cancer", European Journal of Cancer Prevention; Jul. 1999; vol. 8, Issue 3, pp. 213-221.
C. Ghioni, et al; "Polyunsaturated Fatty Acids in Neutral Lipids and Phospholipids of Some Freshwater Insects", Comp. Biochem. Physiol. vol. 114B, No. 2, pp. 161-170; Jun. 1996.
Mingming Huan, et al; "Suicide Attempt and n-3 Fatty Acid Levels in Red Blood Cells: A Case Control Study in China", Biol Psychiatry Feb. 19, 2004; vol. 56; pp. 490-496.
Ewa Kamler, et al; "Fatty acid composition, growth and morphological deformities in juvenile cyprinid, *Scardinius erythrophthalmus* fed formulated diet supplemented with natural food", Aquaculture, Jun. 10, 2008; vol. 278, pp. 69-76.
Penny M. Kris-Etherton, et al; "Fish Consumption, Fish Oil, Omega-3 Fatty Acids, and Cardiovascular Disease" American Heart Association Circulation; 2002; vol. 106; pp. 2747-2757.
Walter J. Lukiw, et al; "A role for docosahexaenoic acid-derived neuroprotection D1 in neural cell survival and Alzheimer disease", The Journal of Clinical Investigation, Oct. 2005, vol. 115, No. 10, pp. 2774-2783; http://www.jci.org.
Alister S. McGill, et al; "A Study of the Composition of Fish Liver and Body Oil Triglycerides", Lipids, vol. 27, No. 5, May 1, 1992, pp. 360-370.
James M. McKenney, et al; "Prescription omega-3 fatty acids for the treatment of hypertrilyceridemia", Am. Journal Health-System Pharmacists, vol. 64, Mar. 15, 2007; pp. 595-605.
Mohammed H. Moghadasian; "Advances in Dietary Enrichment with N-3 Fatty Acids", Critical Reviews in Food Science and Nutrition, vol. 48; Jun. 2008, vol. 48, pp. 402-410.
Victor Mitrano; "Disparate projections for fish meal and oil in 2008", online at: www.pescaaldia.cl/articulos/?id=107 ; 3 pages.
Artemis P. Simopoulos; "Omega-3 fatty acids in wild plants, nuts and seeds", Asia Pacific J. Clin Nutr; vol. 11, Issue Supplement S6, pp. S163-S173; Article first published online: Sep. 26, 2002.
Sophie St-Hilaire, et al; "Fish Offal Recycling by the Black Soldier Fly Produces a Foodstuff High in Omega-3 Fatty Acids", Journal of the World Aquaculture Society, vol. 38, No. 2, Jun. 2007, pp. 309-313.
Sophie St-Hilaire, et al; Fly Prepupae as a Feedstuff for Rainbow Trout, *Oncorhynchus mykiss*; Journal of the World Aquaculture Society, Mar. 2007, vol. 38, No. 1, pp. 59-67.
Kamen Stefanov, et al; "Lipids and sterols in *Musca domestica* L. (Diptera, Muscidae): changes after treatment with sucrose and lead", Comparative Biochemistry and Physiology Part B 131, 2002; pp. 543-550.

(Continued)

*Primary Examiner* — Deborah D Carr
(74) *Attorney, Agent, or Firm* — Ladas & Parry LLP

(57) ABSTRACT

Extract of oil rich in saturated, monounsaturated and polyunsaturated fatty acids containing oil extracted from insect larvae comprising saturated, MUFA and PUFA fatty acids and procedure for obtaining oil extract.

31 Claims, No Drawings

(56) References Cited

OTHER PUBLICATIONS

Alma Y Salazar-Govea, et al; "Fatty Acid supercritical extraction of larva of housefly, *Musca domestica*", 2007; 11 pages.

United States Environmental Protection Agency; "EPA: Proceedings of the 2007 National Forum on Contaminants in Fish" EPA-823-R-07-008; Sep. 2007; 35 pages; All sections of the 2007 Proceedings are available from web site at http://www.epa.gov/waterscience/fish/forum/2007/.

Artemis P. Simopoulos, et al; "Purslane: A Terrestrial Source of Omega-3 Fatty Acids", New England Journal of Medicine; vol. 315, No. 13, p. 833; Sep. 25, 1986.

International Search Report: mailed Oct. 22, 2010; International Application No. PCT/CL2010/000022.

* cited by examiner

OBTAINING FATTY ACIDS FROM INSECT LARVAE

The n-3 fatty acids, popularly called omega-3 fatty acids, are a family of unsaturated fatty acids which are considered to be more typical of alpha linolenic acid (ALA, 18:3, n-3), eicosapentaenoic acid (EPA, 20:5, n-3) and docosahexaenoic acid (DHA, 22:6, n-3). Omega-6 fatty acids (like gamma linolenic acid (18:3, n-6)) and arachidonic acid (20:4, n-6) also exist. There are also generically-named PUFAs, (polyunsaturated fatty acids). The term "n-3" or "omega-3" is used to denote the double bond that exists as the third carbon-carbon from the methyl end of the molecule. The terms omega-7 and omega-9 have also been coined for the whole monounsaturated fatty acids family or MUFA.

The biological significance of molecules like the omega-3 and omega-6 fatty acids prove to be nutritionally essential since at the biological and physiological level they are biomolecule precursors of great importance for the proper functioning of the organism, among which can be mentioned prostaglandins, now known as eicosanoids, as well as thromboxanes, prostacyclins and leukotrienes; all the important molecules in numerous metabolic and biochemical functions of the biological systems. These molecules participate in inflammatory and blood coagulation processes, for which they can be directly related to diseases such as: arthritis, platelet disorders and other blood disorders, lupus and asthma, among others.

The benefits of ingested food for your health are reflected in the circulatory and cardiovascular system, in cholesterol and triglyceride levels, in depressive disorder, in cancer, atherosclerosis and diabetes, among many others.

For a healthy diet, ingesting fish and fish oil is recommended since they contain the fatty acids omega-3, eicosapentaenoic acid (EPA) and docosahexaenoic acid (DHA) (Moghadasian, 2008). These fatty acids are the precursors of eicosanoids, which reduce inflammation and improve functionality of the vascular and nervous systems among many other health benefits (McKenney & Sica 2007, Kris-Etherton et al. 2002, De Deckere, 1999). Recent studies have suggested that fish oil can affect depression, and this is important, risk of suicide (Huan et al. 2004). One of these studies took blood samples from 100 patients who staged suicide attempts and they compared the blood samples with the controls and found that the levels of eicosapentaenoic acid (EPA) were significantly lower in patients who attempted suicide. On one hand, a study showed that omega-3 exerts neuroprotective action in Parkinson's disease. Using an experimental model, it shows a protective effect (just as it did for Alzheimer's disease) (Bousquet et al. 2007, Lukiw, 2005). According to these results, the American Heart Association recommends the consumption of 1 g of fish oil each day, preferably the consumption of the corresponding ratio of fish, in patients with heart disease (American Heart Association, 2007).

The food chain of the fish makes our diet, by containing fish meat, exhibit a healthy omega-3 fatty acid content. Fish such as mackerel, trout, tuna and salmon have high levels of omega-3 fatty acids, however, due to its position in the upper part of the food chain, these species can accumulate toxic substances (biomagnification). For this reason, the FDA (Administración de Alimentos y Medicamentos) recommends limiting the consumption of particular species of fish (predators, for example, tuna, shark and swordfish), due to the high levels of toxic contaminants like mercury, dioxins, PCB and chlordane (EPA (Environmental Protection Agency), 2007).

On the other hand, the fact that predator fish cannot produce omega-3, and therefore they obtain it from their food, makes omega-3 an important raw material in commercial fish breeding worldwide.

The nutraceutical tendency of using supplements of fish oil for obtaining sufficient omega-3 fatty acids in a balanced diet exists which are called sound diets or intelligent diets. In the last few years fish oil supplements have been studied since alarming levels of PCB or other noxious agents have been reported. This has triggered the search and implementation of purification technologies of the products in the production processes of fish oils and extracts.

The majority of fish oils originate from countries like Peru and Chile. This is driven by the high omega-3 content that fish from these areas present, which is almost 30%, in comparison to other areas like Scandinavian countries and other fish oils (around 20%). Those fish oils are being used at an industrial level for producing pharmaceutical and nutraceutical products. Nevertheless, the increased production and consumption of omega-3s continues to be the diet of breeding fish (salmon, trout, others). Although there are omega-3 productions from some microalgae and microbial sources, these are very small in comparison to the large quantities that the fishing industry generates annually.

The production of fish oil worldwide is led by countries like Peru, Denmark, Spain, Chile, Iceland and Norway. Nevertheless, it is globally known that production has declined since 2004, recording a low around 12% between 2004 and 2005, which has been maintained to date. On the other hand, while fish flour decreased its price between 2007 and 2008, fish oil doubled its price in the same period (http://www.pescaaldia.cl/articulos/?id=107), the same as has been described in the case of vegetable oil, which has presented a constant increase in its price.

The main dietary sources of polyunsaturated fatty acids are varied, being, in order of content of these compounds, predominantly the fish (fish oil), flax seeds (linseed oil), eggs and other microalgae oils, zooplankton and microorganisms (uncommon).

On the other hand, it is publicly known that global productions of fish flour and also fish oil have declined in the last few years, marking a downward trend that is sustained. Furthermore, the growing use of vegetable oils in the manufacturing of biofuels and the additional scarcity of monounsaturated (omega-7 and omega-9, or MUFA) and polyunsaturated (mainly omega-3 and omega-6, PUFA) fatty acid sources, reflect and define a supply problem of this type of molecule.

The invention relates to the production of mono and polyunsaturated fatty acids, MUFA and PUFA, respectively. The invention is based on the extraction of high quality oil from insect larvae, constituting a new source of oil and in particular a type of oil rich in unsaturated fatty acids, being, in turn, a sustainable source very different from the marine resources shown today. The fundamental purpose of the invention is to constitute an innovative and alternative form of obtaining unsaturated oils and fatty acids.

DESCRIPTION OF THE INVENTION

The main problem that solves the present invention is generating and obtaining monounsaturated (omega-7 and omega-9, or MUFA) and polyunsaturated (mainly omega-3 and omega-6, or PUFA) fatty acids, added to the possibility of generating oils concentrated in monounsaturated and polyunsaturated fatty acids through the use of different fusion points to achieve its separation. In this context, the invention solves the following:

It provides a production process of raw material rich in monounsaturated fatty acid (omega-7 and omega-9, or MUFA) content.

It provides a production process of raw material rich in polyunsaturated fatty acid (omega-3 and omega-6, or PUFA).

It provides a supply control of raw material since it permits controlling its production.

It provides obtaining rich fatty acid oils through a simple, inexpensive and fast extraction method.

It allows obtaining oils with high concentrations of monounsaturated and polyunsaturated fatty acids since the oil procurement method considers concentration steps of this type of fatty acid.

The present invention refers to the extraction of the fat and lipid fraction that insect larvae contain. In this case, working with housefly (*Musca domestica*) larvae has been selected, which have been raised on an appropriate substrate for their development. The gathering or collecting of the larvae is done in a determined moment of the life cycle of the insect, in a manner which favors the larger content of the molecules that are of interest for oil extraction.

The fly selected for the effectuation of the present invention belongs to the Phylum: Arthropoda, Class: Insect, Order: Diptera, Suborder: Cyclorrhapha, Superfamily: Muscoidea, Family: Muscidae, Genus: *Musca*, Species: Housefly. The lifecycle of this fly consists of the following stages: each female can leave close to 500 eggs in groups. The eggs are white and are approximately 1.2 mm in length. The maximum production of eggs occurs at intermediate temperatures, comprised between 10 and 40° C. In the course of 8 to 20 hours on the first day the larvae hatch from the eggs: they live and are fed as a general rule on organic detritus such as garbage or feces. They have a pale whitish or yellowish color and are 3-12 mm long. They are slender, have a mouth and do not have feet. The optimal temperature for larval development is 35 to 38° C. The larvae complete their development in a period of 4 to 13 days in optimal temperatures or it takes 14 to 30 days in temperatures of 12 to 17° C. Nutrient-rich substrates such as artificial substrates like animal feed consisting of protein-rich vegetable flours and animal flours, substrates based on vegetable scraps and leftovers from meat processing plants, or substrates based on animal manure provide an excellent larval development substrate. Considering animal manure as a model, it requires a small quantity of fecal matter for larval development. At the end of the larval stage, they change into red- or brown-colored pupae and are 8 mm long. The pupae complete their development in a period of 2 to 6 days in a temperature comprised of 32 to 37° C. or it takes 17 to 27 days at a temperature of around 14° C. After the incubation period in the pupa state, in which metamorphosis occurs, they emerge from the pupa state into an adult fly.

For the invention, the larval state of bred flies or insects is especially important, specifically adult larvae or prior to the pupa state or also growing or recently developed pupae. This is important because in all insects whose lifecycle includes a pupa state, this state represents the only state in which they do not ingest food. Therefore, the larvae must store high quality fats and lipids rich in calories in order to be able to induce and sustain metamorphosis until becoming an emerging adult. In order to carry out the extraction of oil rich in omega-7, omega-9 (MUFA), and omega-3, omega-6 (PUFA) molecules, which is the main purpose of the invention, the following main steps must be addressed:

1. Establish a fly breeding system on an appropriate substrate for this purpose.
2. Gather mature larvae, growing pupae or recently developed pupae.
3. The collected material can be stored under freezing conditions.
4. Dehydrate the gathered larvae and pupae.
5. Grind the dehydrated material.
6. Extract the oils with an extractant solvent.
7. Evaporate and/or recycle the extractant solvent.
8. Store the extracted oil under refrigeration.
9. Optionally add the antioxidant agent extracted oil to improve its preservation over time.
10. Optionally add purification steps of molecules of interest and which are oil components.

Description of the Yield

When the yields of the oil extraction process are calculated, it is possible to declare that:

On a wet foundation, between 3-5% by weight of the mass of larvae gathered is extractable oil.

On a dry foundation, between 13-16% by weight of the dehydrated material corresponds to extractable oil.

Percentage variations are due to the substrate on which the larvae are raised, but mainly due to the maturity state in which the larvae are gathered or collected since if during collection mature or pre-pupae larvae are predominantly obtained, the oil content is the optimal possible to obtain. This contrasts with the case in which recently developed pupae are collected, a situation in which the oil content begins to decline.

The typical percentage composition that the obtained oil describes is 15% of saturated fatty acids, 40% of monounsaturated fatty acids and 27% of polyunsaturated fatty acids, which are comparable and improved values in nutritional quality with respect to fish oils and other sources that currently exist in the market.

Description of the Oil (Analysis)

The invention shows a typical composition in regard to the type and percentage of fatty acids the oil composes.

With regard to this matter, Table 1 shows the saturated fatty acid content, Table 2, the monounsaturated fatty acid content, and Table 3 the polyunsaturated fatty acid content.

TABLE 1

Saturated fatty acid content in the oil.

| Saturated Fatty Acids | % Methyl Ester | g/100 g | mg/100 g |
| --- | --- | --- | --- |
| C12: 0 Dodecanoic Acid | 0.115 | 0.093 | 93.349 |
| C14: 0 Tetradecanoic Acid | 3.220 | 2.606 | 2605.994 |
| C16: 0 Palmitic Acid | 11.981 | 9.696 | 9696.014 |
| C18: 0 Stearic Acid | 2.477 | 2.004 | 2004.420 |
| C20: 0 Eicosanoic Acid | 0.167 | 0.135 | 135.118 |
| C22: 0 Docosanoic Acid | 0.056 | 0.045 | 45.416 |
| C24: 0 Tetracosanoic Acid | 0.081 | 0.065 | 65.288 |
| Total Saturated Fatty Acids | 18.097 | 14.646 | 14645.601 |

TABLE 2

Monounsaturated fatty acid content in the oil.

| Monounsaturated Fatty Acids | % Methyl Ester | g/100 g | mg/100 g |
| --- | --- | --- | --- |
| Omega-7 | | | |
| C16: 1 Palmitoleic Acid | 17.323 | 14.019 | 14019.089 |
| Omega-9 | | | |
| C14: 1 Tetradecenoic Acid | 0.382 | 0.309 | 309.339 |
| C18: 1 Oleic Acid | 28.602 | 23.147 | 23147.381 |
| C20: 1n9 Eicosaenoic Acid | 2.083 | 1.686 | 1685.644 |

TABLE 2-continued

Monounsaturated fatty acid content in the oil.

| Monounsaturated Fatty Acids | % Methyl Ester | g/100 g | mg/100 g |
|---|---|---|---|
| C22: 1n9 Erucic Acid | 0.194 | 0.157 | 156.763 |
| C24: 1 Tetracosanoic Acid | 0.258 | 0.209 | 209.135 |
| Total Monounsaturated Fatty Acids | 48.842 | 39.527 | 39527.350 |

TABLE 3

Polyunsaturated fatty acid content in the oil.

| Polyunsaturated Fatty Acids | % Methyl Ester | g/100 g | mg/100 g |
|---|---|---|---|
| Omega-3 | | | |
| C18: 3n3 Linolenic Acid (ALA) | 0.549 | 0.444 | 444.457 |
| C20: 5n3 Eicosapentaenoic Acid (EPA) | 15.942 | 12.902 | 12901.810 |
| C22: 6n3 Docosahexaenoic Acid (DHA) | 9.998 | 8.091 | 8090.989 |
| Omega-6 | | | |
| C18: 2n6 Linoleic Acid | 2.364 | 1.913 | 1912.946 |
| C18: 3n6 Linolenic Acid | 0.000 | 0.000 | 0.000 |
| C20: 2n6 Eicosadienoic Acid | 0.151 | 0.122 | 121.848 |
| C20: 3n6 Eicosatrienoic Acid | 0.000 | 0.000 | 0.000 |
| C20: 3n3 Eicosatetrienoic Acid | 0.000 | 0.000 | 0.000 |
| C20: 4n6 Eicosatetraenoic Acid | 1.131 | 0.915 | 915.100 |
| C22: 5n3 Docosapentaenoic Acid | 2.928 | 2.369 | 2369.189 |
| Total Polyunsaturated Fatty Acids | 33.061 | 26.756 | 26756.339 |

Description of the Elaboration Process
Breeding Flies

Flies can be bred on different substrates which can be selected from manure (human and/or animal), organic residue, biotreatment or bioconversion of urban runoff, wheat bran, decomposing vegetable scraps, and a mixture of these. Fly breeding systems have been described and there are some patented which is why the present invention does not examine any aspect of fly breeding. Nevertheless, the collection of mature larvae and recently developed pupae compose a key point in obtaining the raw material for the extraction of oil rich in monounsaturated and polyunsaturated fatty acids. In this sense, the use of certain states of the lifecycle of flies constitutes part of the invention.

Dehydration

Once the larvae and pupae are collected and established in a fly breeding system, they must be dehydrated. Prior to the dehydration step, temporary storage of the larvae and pupae being necessary, the storage must be carried out under freezing conditions (refrigeration below 0° C.). The dehydration process is accomplished by incubating them at 60° C. for 16 to 24 hours. This process can be achieved in an electrical heating oven with good ventilation or also in a dehydration system based on the flow of hot air.

Extraction

The dehydrated material is ground in a mill; on a laboratory scale this can be achieved in a manual kitchen grinder or blender while on an industrial scale it can be achieved using a mill similar to that used in manufacturing flour from grains or by using industrial grinding equipment. The ground material is disposed in appropriate quantities for the size of the extraction system that is being used. The extraction is carried out with a Soxhlet system, in which it is possible to use hexane or other pure organic solvents, or an extractant mixture composed of hexane and dichloromethane in a ratio that can be 1:1, 1:2 or more often 3:1; this mixture improves the extraction of moderately polar and polar molecules. The preparation of extractant and material to be extracted must have a ratio of 50 g of crushed material per 250 mL of extractant blend (200 g/L).

Extraction is achieved using 8 to 10 extraction cycles (in siphons) of boiling extractant through ground material. After the ground material is separated and the extractant residue is evaporated, it is recovered by distillation which is why this material rich in proteins and carbohydrates can be used as a food source.

Afterward, the extractant comprising the extracted oil is subjected to a simple distillation for separating it from the oil. With this process the extractant is recovered in order to be reused and the pure oil free of extractant is obtained. After this distillation, the oil is left to cool to room temperature for a period of 8 to 16 hours, finally providing the oil extract of the present invention.

Storage

The obtained pure oil can be preserved bottled for long periods by adding an antioxidant.

Description of Application and Functionality

The comparison of vegetable oil, fish oil and the concentrations that are usually obtained for each type of fatty acid of the present invention is described in Table 4.

TABLE 4

Comparison of fatty acid percentages present in different oils.

| COMPOSITION PERCENTAGE (%)[1, 2] Oil from | | | | | COMPONENT |
|---|---|---|---|---|---|
| Sunflower | Rap | Fish | Invention | | Fatty Acids |
| 12% | 7% | 37% | 11%-16% | 15% | Saturated |
| 13% | 59% | 21% | 32%-42% | 40% | Monounsaturated |
| Not present | Not present | 30% | 25%-30% | 27% | Polyunsaturated* |

*Only the EPA + DHA Content is compared as Polyunsaturated.

REFERENCES

1. Simopoulos A. P., Salem N. Jr. (1989). Purslane: a terrestrial source of omega-3 fatty acids. N. Engl. J. Med. 315, 833.
2. McGill A. S. & Moffat C. F. (1992). A Study of the Composition of Fish Liver and Body Oil Triglycerides. Lipids. Vol. 27, No. 5.360-370.

The oils rich in omega-3 and omega-6 as well as omega-7 and omega-9, as is the case with larval oil, cause for the present invention, are widely used in the pharmaceutical industry as compounds that help to decrease numerous degenerative diseases. The food and nutraceutical industry uses them in an increasing manner as foodstuff supplements in healthy diets and complementary diets for treatment procedures of illnesses or as healthy and functional food.

On the other hand, one of the major applications of monounsaturated and polyunsaturated fatty acids is in the diet of farm animals. This is because they improve the quality of fish, poultry and pig meat, the quality of cow milk and the fat quality and composition of eggs in addition to improving the sanitary conditions of the previously mentioned animals.

The oil extracted from larvae proves to be very attractive when compared to fish oil, most widely used as a raw material, as a reference point for other oils since it has a lower saturated fatty acid content, higher monounsaturated fatty acids content (double), and similar polyunsaturated fatty acid content. Therefore, the applications of this oil can be infinite.

Finally, it is important to mention that there are described and patented chemical procedures for enriching polyunsaturated fatty acids in fish oils as well as chemical mechanisms and protocols for achieving purification of different fractions present in a raw extract, like the saturated, monounsaturated and polyunsaturated fatty acid fractions. In this context, larvae oil will allow itself to be used as a raw material for achieving pure fractions from the different types of fatty acids, this composing an additional application to the environment on a chemical industrial scale with wide applications of subproducts in the food, pharmaceutical and nutraceutical industries, among others.

REFERENCES

1. Moghadasian M H. May 2008. "Advances in dietary enrichment with n-3 fatty acids". *Critical Reviews in Food Science and Nutrition* 48 (5): 402-10. DOI:10.1080/10408390701424303. PMID 1846-4030.
2. Kris-Etherton P. M, Harris W. S, Appel L. J. (2002). Fish Consumption, Fish Oil, Omega-3 Fatty Acids, and Cardiovascular Disease. *Circulation* 2002; 106; 2747-2757. DOI: 10.1161/01. CIR.0000038493.65177.94.
3. McKenney J. M. & Sica D. (2007). "Prescription omega-3 fatty acids for the treatment of hypertriglyceridemia". *American Journal of Health-System Pharmacy* 64 (6): 595-605. PMID 17353568.
4. De Deckere, E. A. (1999). "Possible beneficial effect of fish and fish n-3 polyunsaturated fatty acids in breast and colorectal cancer". *European Journal of Cancer Prevention* 8 (3): 213-221. PMID 10443950.
5. Huan M, Hamazaki K, Sun Y, Itomura M, Liu H, Kang W, Watanabe S, Terasawa K, Hamazaki T. (2004). "Suicide attempt and n-3 fatty acid levels in red blood cells: a case control study in China". *Biological psychiatry* 56 (7): 490-6. D01:10.1016/j.biopsych. Jun. 6, 2004. PMID 1540784.
6. Bousquet M, Saint-Pierre M, Julien C, Salem N. Jr., Cicchetti F, Calon F. (2007). "Beneficial effects of dietary omega-3 polyunsaturated fatty acid on toxin-induced neuronal degeneration in an animal model of Parkinson's disease". *The Federation of American Societies for Experimental Biology* 22: 1213. doi:10.1096/fj.07-9677com. PMID 18032633.
7. Lukiw W. J. (2005). "A role for docosahexaenoic acid—derived neuroprotectin D1 in neural cell survival and Alzheimer disease". *J. Clin. Invest* 115: 2774-2783. doi: 10.1172/JCI25420. Feb. 9, 2007.
8. American Heart Association. Feb. 9, 2007. "Fish and Omega-3 Fatty Acids".

The invention claimed is:

1. An extract of oil from fly larvae and pupae comprising saturated, monounsaturated and polyunsaturated fatty acids, the content of which equals 11-16%, 32-42% and 25-30% respectively in the final composition of oil.

2. The extract of oil according to claim 1, wherein the oil extracted from fly larvae comprises saturated, monounsaturated and polyunsaturated fatty acids, the content of which equals 15%, 40% and 27% respectively in the final composition of oil.

3. The extract of oil according to claim 1, wherein the saturated fatty acids are composed of C12:0 dodecanoic acid, C14:0 tetradecanoic acid, C16:0 palmitic acid, C18:0 stearic acid, C20:0 eicosanoic acid, C22:0 docosanoic acid, and C24:0 tetracosanoic acid.

4. The extract of oil according to claim 3, wherein the content of C12:0 dodecanoic acid is 0.093 g/100 g of oil extract.

5. The extract of oil according to claim 3, wherein the content of C14:0 tetradecanoic acid is 2.606 g/100 g of oil extract.

6. The extract of oil according to claim 3, wherein the content of C16:0 palmitic acid is 9.696 g/100 g of oil extract.

7. The extract of oil according to claim 3, wherein the content of C18:0 stearic acid is 2.004 g/100 g of oil extract.

8. The extract of oil according to claim 3, wherein the content of 020:0 eicosanoic acid is 0.135 g/100 g of oil extract.

9. The extract of oil according to claim 3, wherein the content of C22:0 docosanoic acid is 0.045 g/100 g of oil extract.

10. The extract of oil according to claim 3, wherein the content of C24:0 tetracosanoic acid is 0.065 g/100 g of oil extract.

11. The extract of oil according to claim 1, wherein the monounsaturated fatty acids are composed of omega-7 and omega-9 fractions, the omega-7 fraction corresponding to C16:1 palmitoleic acid, and the omega-9 fraction containing C14:1 tetradecenoic acid, C18:1 oleic acid, C20:1n9 eicosaenoic acid, C22:1n9 erucic acid and C24:1 tetracosanoic acid.

12. The extract of oil according to claim 11, wherein the content of 016:1 palmitoleic acid is 14.019 g/100 g of oil extract.

13. The extract of oil according to claim 11, wherein the content of C14:1 tetradecenoic acid is 0.309 g/100 g of oil extract.

14. The extract of oil according to claim 11, wherein the content of C18:1 oleic acid is 23.147 g/100 g of oil extract.

15. The extract of oil according to claim 11, wherein the content of C20:1n9 eicosaenoic acid is 1.686 g/100 g of oil extract.

16. The extract of oil according to claim 11, wherein the content of C22:1 n9 erucic acid is 0.157 g/100 g of oil extract.

17. The extract of oil according to claim 11, wherein the content of C24:1 tetracosanoic acid is 0.209 g/100 g of oil extract.

18. The extract of oil according to claim 1, wherein the polyunsaturated fatty acids are composed of omega-3 and omega-6 fractions, the omega-3 fraction containing: C18:3n3 linolenic acid, C20:5n3 eicosapentaenoic acid and C22:6n3 docosahexaenoic acid and wherein the omega-6 fraction contains: C18:2n6 linoleic acid, C20:2n6 eicosadienoic acid, C20:4n6 eicosatrienoic acid, and C22:5n3 docosapentaenoic acid.

19. The extract of oil according to claim 18, wherein the content of C18:3n3 linolenic acid (ALA) is 0.444 g/100 g of oil extract.

20. The extract of according to claim 18, wherein the content of C20:5n3 eicosapentaenoic acid is 12.902 g/100 g of oil extract.

21. The extract of oil according to claim 18, wherein the content of C22:6n3 docosahexaenoic acid is 8.091 g/100 g of oil extract.

22. The extract of oil according to claim 18, wherein the content of C18:2n6 linoleic acid is 1.913 g/100 g of oil extract.

23. The extract of oil according to claim 18, wherein the content of C20:2n6 eicosadienoic acid is 0.122 g/100 g of oil extract.

24. The extract of oil according to claim 18, wherein the content of C20:4n6 eicosatrienoic acid is 0.131 g/100 g of oil extract.

25. The extract of oil according to claim 18, wherein the content of C22:5n3 docosapentaenoic acid is 2.369 g/100 g of oil extract.

26. A process of obtaining an extract of fly larvae and pupae rich in saturated, monounsaturated and polyunsaturated fatty acids, said process comprising the steps of:
   breeding flies, on a substrate selected from the group consisting of manure, organic residue, biotreatment or bioconversion of urban runoff, wheat bran, decomposing vegetable scraps and mixtures thereof at a temperature of between 10 and 40° C., permitting growth to reach larval development;
   collecting the developed larvae and pupae in fly breeding,
   dehydrating the collected larvae and pupae in an electric heating system with ventilation or in a dehydration system based on the flow of hot air,
   grinding the dehydrated material in a grinder,
   extracting the ground, dehydrated material from the previous step with a Soxhlet system using pure organic solvents, hexane, or a mixture of hexane:dichloromethane 1:1 or 1:2 or 3:1 in a ratio of 50 g of ground material per 250 mL of extractant blend as a solvent,
   repeating the extracting step for 8 to 10 extraction cycles,
   separating the ground material,
   evaporating the extractant residue,
   recovering through distillation,
   distilling the extractant containing the extracted oil to separate it from the oil,
   obtaining the pure oil free of extractant,
   allowing it to cool to room temperature for a period of 8 to 16 hours,
   optionally adding an antioxidant, and
   storing the product,
wherein,
   the larvae and pupae developed in the breeding of flies are selected from mature larvae and recently developed pupae and
   said extract is an extract of mature larvae and recently developed pupae.

27. The extract of oil according to claim 2, wherein the saturated fatty acids are composed of C12:0 dodecanoic acid, C14:0 tetradecanoic acid, C16:0 palmitic acid, C18:0 stearic acid, C20:0 eicosanoic acid, C22:0 docosanoic acid, and C24:0 tetracosanoic acid.

28. The extract of oil according to claim 2, wherein the monounsaturated fatty acids are composed of omega-7 and omega-9 fractions, the omega-7 fraction corresponding to C16:1 palmitoleic acid, and the omega-9 fraction containing C14:1 tetradecenoic acid, C18:1 oleic acid, C20:1n9 eicosaenoic acid, C22:1n9 erucic acid and C24:1 tetracosanoic acid.

29. The extract of oil according to claim 2, wherein the polyunsaturated fatty acids are composed of omega-3 and omega-6 fractions, the omega-3 fraction containing: C18:3n3 linolenic acid, C20:5n3 eicosapentaenoic acid and C22:6n3 docosahexaenoic acid and wherein the omega-6 fraction contains: C18:2n6 linoleic acid, C20:2n6 eicosadienoic acid, C20:4n6 eicosatrienoic acid, and C22:5n3 docosapentaenoic acid.

30. The extract of oil according to claim 1, wherein said fly is *Musca domestica*.

31. The process according to claim 26, wherein said fly is *Musca domestica*.

* * * * *